United States Patent [19]

Wedig et al.

[11] Patent Number: 4,610,993

[45] Date of Patent: * Sep. 9, 1986

[54] USE OF SELECTED PYRIDINE-N-OXIDE DISULFIDE COMPOUNDS TO TREAT OR PREVENT BOVINE MASTITIS

[75] Inventors: John H. Wedig, Guilford, Conn.; John G. Babish, Ithaca, N.Y.; Jeffrey Davidson, Tulare, Calif.

[73] Assignee: Olin Corporation, Cheshire, Conn.

[ * ] Notice: The portion of the term of this patent subsequent to Aug. 30, 2000 has been disclaimed.

[21] Appl. No.: 638,808

[22] Filed: Aug. 8, 1984

[51] Int. Cl.[4] .............................................. A61K 31/44
[52] U.S. Cl. ................................................... 514/335
[58] Field of Search ......................................... 514/335

[56] References Cited

U.S. PATENT DOCUMENTS

| | | | |
|---|---|---|---|
| 3,818,018 | 6/1974 | Weisse et al. | 260/294.8 J |
| 3,890,434 | 6/1975 | Weisse et al. | 424/70 |
| 4,401,666 | 8/1983 | Wedig et al. | 424/245 |

*Primary Examiner*—Frederick E. Waddell
*Attorney, Agent, or Firm*—William A. Simons; Thomas P. O'Day

[57] ABSTRACT

Described is a method for treating an animal for bovine mastitis wherein said animal is administered an effective amount of at least one selected pyridine-N-oxide disulfide compound to treat or prevent bovine mastitis.

8 Claims, No Drawings

USE OF SELECTED PYRIDINE-N-OXIDE DISULFIDE COMPOUNDS TO TREAT OR PREVENT BOVINE MASTITIS

BACKGROUND OF THE INVENTION

1. Field of the Invention

This invention relates to the use of selected pyridine-N-oxide disulfide compounds to prevent or treat bovine mastitis.

2. Description of the Prior Art

Bovine mastitis is an infection of the udder of ruminants such as cows, mainly caused by gram positive bacteria and especially in cows in intensive milk producing units. It results in the inflammation of the mammary gland (i.e., teats and udder). The disease is particularly troublesome and of considerable economic importance because the pathogen is readily transferred from one animal to another during the milking process. Some of the main pathogens causing bovine mastitis are *Staphylococcus aureus, Streptococcus agalactiae, Streptococcus uberis, Streptococcus dysgalactiae, Escherichia coli, Aerobacter aerogenes, Klebsiella pneumoniae,* and *Pseudomonas aeruginosa.*

Effective compounds to be used in the treatment or prevention of bovine mastitis should give the following results:

1. Most or all of the above pathogens should be susceptible to the compound when the latter is in milk and other udder fluids.

2. The therapeutic effect should be relatively quick.

3. No significant irritation should be caused to the teats or udder of the cow, either by the active compound or other ingredients used with it.

4. The active compound should not stay in the milk for a period much in excess of the one required for the therapeutic activity so as to minimize the loss of milk, which has to be discarded when as an undesired foreign compound is present.

There are other requirements for such a composition for the treatment of bovine mastitis but the above four criteria are some of the most important ones.

Bovine mastitis has so far been treated mainly by administering anti-microbial agents such as antibiotics, e.g. Penicillin G, Dihydrostreptomycin, and the like. However, it has been recently found to be very desirable to replace antibiotics by non-antibiotic drugs. The following are some reasons why:

1. Antibiotics effective in human medicine should not be utilized in veterinary medicine, in order not to build up a strain resistance against bacteria appearing in human diseases.

2. *Staphylococcus aureus,* one of the above-noted pathogens, has already built up a resistance against most of the antibiotics utilized in the treatment of bovine mastitis.

It thus is very important to find a method for the treatment of bovine mastitis utilizing a nonantibiotic compound which substantially would overcome the desired results as set out above. U.S. Pat. No. 4,401,666, which issued to J. H. Wedig et al on Aug. 30, 1983, claims a method for treating animals for bovine mastitis with at least one metallic salt of pyridine 2-thione-N-oxide. This patent is incorporated herein by reference in its entirety.

BRIEF SUMMARY OF THE INVENTION

The present invention, therefore, is directed to treating an animal for bovine mastitis which comprises administering to said animal an effective amount of at least one pyridine-N-oxide disulfide compound to treat or prevent bovine mastitis, said pyridine-N-oxide disulfide compound selected from (b) 2,2'-dithiobis-pyridine-1,1'-dioxide; and (c) adducts of 2,2'-dithiobis-pyridine-1,1'-dioxide, the adducts having the formula (I):

$$(C_5H_4NOS)_2MY_t \qquad (I)$$

wherein M is an alkaline earth metal selected from the group consisting of calcium, magnesium, barium and strontium; Y is an anion selected from the group consisting of halides, sulfates, nitrates, chlorates and acetates; and t is either 1 or 2.

DETAILED DESCRIPTION

The above-noted pyridine-N-oxide disulfide compounds are well known chemicals which may be made by oxidation of the sodium salt of pyridine-2-thione-N-oxide, preferably with hydrogen peroxide or another oxidizing agent. U.S. Pat. No. 2,742,476, which issued to Bernstein et al on Apr. 17, 1956, discloses 2,2'-dithiobis-pyridine-1,1-dioxide and its preparation. The adducts of 2,2'-dithiobis-pyridine-1,1'-dioxide listed in (b) above and their preparation are described in U.S. Pat. Nos. 3,818,018 and 3,890,434, which issued to Weisse et al on June 18, 1984 and June 17, 1975, respectively. All of these U.S. Patents are incorporated herein by reference in their entireties.

Also included in the adducts are hydrates of the aforementioned compounds of formula (I), i.e. adducts including $nH_2O$ groups where n is an integer of 0 to 10.

The preferred compounds for use in this invention are 2,2'-dithiobis-pyridine-1,1'-dioxide and the magnesium sulfate trihydrate adduct of 2,2'-dithiobis-pyridine-1,1'-dioxide (i.e. M is magnesium, Y is sulfate and t is 1).

In practicing the process of the present invention, ruminant animals such as cows may be treated with an effective bovine mastitis treating amount of at least one pyridine-N-oxide disulfide compound. It is to be understood that the term "an effective amount to treat or prevent bovine mastitis" as used in the specification and claims herein is intended to include any amount or concentration of the above-noted active compounds that will treat or prevent bovine mastitis in such animals. Of course, this amount may be changed in response to numerous variables, such as the degree of effectiveness required, whether animal is milking or dry, and type of carrier, if any.

For most uses, an effective amount to treat or prevent bovine mastitis would be advantageously performed by administering from 1 to about 4 doses comprising from about 25 to about 1000 mg. of the active compound or compounds in intervals from about 12 to about 48 hours into each teat of the animal. Preferably, said doses comprise from about 25 to 100 mg. of 2,2'-dithiobis-pyridine-1,1'-dioxide or its magnesium sulfate trihydrate adduct per dose and said doses are administered about each 12 to 24 hours. Furthermore, the active compound or compounds used in the present process may be combined with other known veterinary and pharmaceutical agents for further benefits.

While the process of the present invention is applicable to the teats of all bovine types of mammals, the major economic impact of bovine mastitis is in connection with dairy cows. Accordingly, the following description of the invention will be concerned mainly with cows; however, it is to be understood that this invention is contemplated with the treatment of all non-human types of mammals.

This step of administering these selected pyridine-N-oxide disulfide compounds to the animal is preferably accomplished in the form of a composition by way of an intramammary infusion; i.e. the composition is injected into the teat through the milk canal. Such compositions would comprise at least one active compound and at least one vehicle or carrier suitable for administration in a bovine udder.

Another preferred way of administering the active compound is by applying it in a teat dip or the like wherein the outside of the teat is covered with an effective amount of the active compound to treat or prevent bovine mastitis.

Sometimes a cow or other ruminant should be treated, as a preventive manner, even if it is not clear whether she suffers from mastitis (i.e. it might be that her udder is healthy). This is important, for instance, in case that it clear that some animals of a herd are suffering from bovine mastitis and then one may want to treat all animals of said herd in order to ascertain that no furhter animals would be infected. Thus, prevention as well as treatment of this disease is contemplated within the scope of the invention.

Moreover, it should be understood that the process of the present invention may be performed with milking cows as well as dry cows. In the case of dry cows, it is desirable that the active compound should stay for a longer time in the udder. This can be achieved by adding a slow release base (e.g., by the employment of a mineral oil or the like with or without a gelling agent as a carrier).

If at least one active compound is combined with a solid or liquid vehicle or carrier before application, then any suitable methods for formulating and applying the active compound or compounds may be employed. Included in such suitable methods of application are emulsifiable liquid solutions, suspensions, creams, and ointments.

Emulsifiable liquids may be prepared by dispersing the active compound in a vegetable oil or mineral oil, such as peanut oil, corn oil, soybean oil, sesame oil and the like, and then admixing the thus formed solution with a suitable surfactant or emulsifier.

Solutions and suspensions are generally formed by dissolving or dispersing the active compound in water or a suitable aqueous solution or other solvent.

Creams and ointments are generally made the same as emulsified liquids except at least one gelling agent or the like is additionally added. Such gelling agents may be natural waxes like beeswax or aluminum fatty acid salts (e.g. stearates, palmitates and oleates).

It should be clearly understood that any of the above-noted formulations, the ingredients which may make up such formulations other than the active compound and its dosage, and means for applying these formulations may include all known and conventional substances, amounts and means, respectively, that are suitable for obtaining the desired bovine mastitis treatment or prevention result. Therefore, such process parameters are not critical to the present invention.

Besides the above-noted active compounds, the present invention also contemplates the use of similar pyridine-2-thione-N-oxide compounds to treat bovine mastitis. Specifically, the present invention contemplates the use of free 2-mercaptopyridine-N-oxide and organic salts (e.g., t-butylamine salt) and adducts of 2-mercaptopyridine-N-oxide. The present invention also contemplates the use of similar compounds which have one or more other substituents on the pyridine ring (e.g., lower alkyl groups, $NO_2$, or halogens).

The following Examples further illustrate the present invention. All parts and percentages are by weight unless explicitly stated otherwise.

EXAMPLE 1

Minimum Inhibitory Concentration (MIC) Values of Magnesium Sulfate Trihydrate Adduct of 2,2'-Dithiobis-pyridine-1,1'-dioxide Required to Inhibit Growth of Microorganisms Isolated from Mastitic Cows Bacterial isolates for these studies were obtained from the New York State Mastitis Control Program, a division of veterinary clinical services of the New York State College of Veterinary Medicine, Cornell University. Samples were from cows with clinical mastitis or from milk cows that were cultured for a routine herd survey. Mastitis pathogens were identified by the use of standard bacteriologic technique[1].

[1]Microbiological Procedures for the Diagnosis of Bovine Mastitis, Washington, D.C., National Mastitis Council, Univ. New Hampshire Press, 1969.

Concentrations inhibiting growth by 50% were determined using broth dilution test procedures[2]. Briefly 0.1 ml of cultures containing approximately $9 \times 10^6$ organisms/ml were inoculated into 10 mls of Tryptose-soy broth[3] containing either 0, 1, 10, 100, or 1000 ppm of zinc pyridine-2-thione-N-oxide. These tubes were incubated at 37° C. for 18 hours and optical densities were read at 550 nanometers. Blanks for each test level consisted of a Tryptose-soy broth tube with the same concentration of test material. Concentrations of test material inhibiting growth by 50% were computed by probit analysis[4].

[2]Ericsson, M. N. and Sherris, M. C. (1971) Antibiotic Sensitivity Testing Report of an International Collaborative Study. *Acta Pathol Microbiol. Scand.* Sect. B., Suppl. 217.
[3]Diffico Manual of Dehydrated Culture Media and Reagents for Microbiological and Clinical Lab Procedures. 9th Edition, Diffico Labs, Inc., Detroit, MI (1977).
[4]Finney, D. J. (1971) Probit Analysis, Cambridge Univ. Press.

The minimum inhibitory concentrations of magnesium sulfate trihydrate adduct of 2,2'-dithiobis-pyridine-1,1'-dioxide for various microorganisms in broth are given in Table 1.

TABLE 1

| Organism | No. of Isolates | 100% by Weight Growth Inhibited |
|---|---|---|
| Staphylococcus aureus | 4 | 1 ppm |
| Streptococcus pyrogenes | 4 | 1 |
| Escherichia coli | 4 | 10 |
| Pseudomonas aeruginosa | 2 | 100–1000 |
| Klebsiella pneumoniae | 4 | 10 |
| Yeast Group | 4 | 10 |

These results indicate that magnesium sulfate trihydrate adduct of 2,2'-dithiobis-pyridine-1,1'-dioxide is effective against microorganisms which cause bovine mastitis. They also indicate that this active compound is especially effective against *E. coli* and *K. pneumoniae*, which cause very severe forms of mastitis that could kill diseased cattle.

What is claimed is:

1. A method of treating an animal for bovine mastitis which comprises administering to said animal an effective amount of at least one pyridine-N-oxide disulfide compound to treat or prevent bovine mastitis, said pyridine-N-oxide disulfide compound selected from the group consisting of
   (a) 2,2'-dithiobis-pyridine-1,1'-dioxide; and
   (b) adducts of 2,2'-dithiobis-pyridine-1,1'-dioxide, the adducts having the formula:

$$(C_5H_4NOS)_2MY_t$$

wherein M is an alkaline earth metal selected from the group consisting of calcium, magnesium, barium and strontium; Y is an anion selected from the group consisting of halides, sulfates, nitrates, chlorates and acetates; and t is either 1 or 2.

2. The method of claim 1 wherein the administration is effected to the teats and udder of a cow.

3. The method of claim 2 wherein from 1 to about 4 doses of about 25 to about 1000 milligrams of 2,2'-dithiobis-pyridine-1,1'-dioxide are infused into each teat of said cow at intervals of 12 to 48 hours.

4. The method of claim 3 wherein from about 25 to about 100 milligrams of said 2,2'-dithiobis-pyridine-1,1'-dioxide are infused into each teat of said cow.

5. The method of claim 2 wherein an effective amount of 2,2'-dithiobis-pyridine-1,1'-dioxide is applied to the outside of the teats and udder of a cow.

6. The method of claim 2 wherein from 1 to about 4 doses of about 25 to about 1000 milligrams of the magnesium sulfate trihydrate adduct of 2,2'-dithiobis-pyridine-1,1'-dioxide are infused into each teat of said cow at intervals of 12 to 48 hours.

7. The method of claim 6 wherein from about 25 to about 100 milligrams of said magnesium sulfate trihydrate adduct of 2,2'-dithiobis-pyridine-1,1'-dioxide are infused into each teat of said cow.

8. The method of claim 2 wherein an effective amount of magnesium sulfate trihydrate adduct of 2,2'-dithiobis-pyridine-1,1'-dioxide is applied to the outside of the teats and udder of a cow.

* * * * *

UNITED STATES PATENT AND TRADEMARK OFFICE
CERTIFICATE OF CORRECTION

PATENT NO. : 4,610,993

DATED : September 9, 1986

INVENTOR(S) : Wedig et al

It is certified that error appears in the above-identified patent and that said Letters Patent is hereby corrected as shown below:

In column 1, at line 59 after "overcome" and before "desired" insert --the drawbacks of antibiotics utilized so far and would give the--.

Signed and Sealed this

Eleventh Day of November, 1986

Attest:

DONALD J. QUIGG

Attesting Officer

Commissioner of Patents and Trademarks